United States Patent
Brotzman et al.

(10) Patent No.: US 9,033,162 B2
(45) Date of Patent: May 19, 2015

(54) SYSTEM, METHOD AND APPARATUS FOR SURGICAL STAND

(71) Applicant: American Medical Stand LLC, Leander, TX (US)

(72) Inventors: Steven B. Brotzman, Austin, TX (US); James H. Esch, Georgetown, TX (US); Timothy A. Marvin, Liberty Hill, TX (US); John V. Witbeck, Leander, TX (US)

(73) Assignee: American Medical Stand LLC, Leander, TX (US)

( * ) Notice: Subject to any disclaimer, the term of this patent is extended or adjusted under 35 U.S.C. 154(b) by 0 days.

(21) Appl. No.: 13/758,411

(22) Filed: Feb. 4, 2013

(65) Prior Publication Data
US 2013/0200023 A1     Aug. 8, 2013

Related U.S. Application Data

(60) Provisional application No. 61/595,928, filed on Feb. 7, 2012.

(51) Int. Cl.
| | | |
|---|---|---|
| *A47F 7/00* | (2006.01) | |
| *A47F 3/14* | (2006.01) | |
| *A61B 19/02* | (2006.01) | |

(Continued)

(52) U.S. Cl.
CPC .............. *A61B 19/0256* (2013.01); *A47F 5/04* (2013.01); *A47B 87/0261* (2013.01); *A61B 19/0248* (2013.01); *A61B 19/0271* (2013.01); *A61B 2019/0251* (2013.01); *A61B 2019/0255* (2013.01)

(58) Field of Classification Search
CPC ........... A61B 19/0256; A61B 19/0248; A61B 2019/0251; A61B 2019/0255; A61B 19/0271; A61B 2019/0258; A61B 2019/0259; A61B 2019/0278; A61B 2019/0279; A61B 2019/0285; A61B 2019/0286; A61B 2019/025; A61B 2019/48; A61B 2019/4868; A61B 19/02; A61B 19/026; B25H 3/04; B25H 3/06; A47G 23/02; A47F 3/14; A47F 5/0018; A47F 5/0025; A47F 7/145; A47F 5/0062; A47F 5/137; A47F 7/144; A47F 5/04; A47F 5/106; A47F 5/05; A47B 23/04; A47B 13/14; A47B 31/00; A47B 87/0261; A47B 57/045; A47B 2031/006; F16L 3/223; A61L 2/26
USPC ............. 211/107, 85.13, 196, 205, 13.1, 175, 211/70.6, 128.1, 126.14, 119.006, 119.007, 211/133.1, 133.3; 248/128, 129, 133; 433/79; 108/92, 93, 49, 50, 147.11, 108/147.12; 206/363, 364, 366, 368, 369, 206/370
See application file for complete search history.

(56) References Cited

U.S. PATENT DOCUMENTS

| | | | |
|---|---|---|---|
| 2,709,818 A | | 6/1955 | Freese |
| 3,301,406 A | * | 1/1964 | Scott .......................... 211/88.01 |

(Continued)

FOREIGN PATENT DOCUMENTS

| | | |
|---|---|---|
| GB | 26265 | 0/1903 |

*Primary Examiner* — Jennifer E Novosad

(57) ABSTRACT

A surgical stand has a support post in a substantially vertical orientation. A frame extends from the support post in a substantially horizontal orientation. A disposable tray has a first deck that rests on and is supported by the frame. A second deck is connected to and transversely spaced apart from the first deck, such that at least lateral access to both the first and second support surfaces is provided.

18 Claims, 10 Drawing Sheets

(51) Int. Cl.
*A47F 5/04* (2006.01)
*A47B 87/02* (2006.01)

(56) References Cited

U.S. PATENT DOCUMENTS

| | | | |
|---|---|---|---|
| D248,871 S | 8/1978 | Forsman et al. | |
| 4,122,956 A * | 10/1978 | Hargrove | 211/126.14 |
| D261,837 S | 11/1981 | Sonder et al. | |
| D270,588 S | 9/1983 | Kemple | |
| 4,445,859 A * | 5/1984 | Hoffmeister et al. | 433/79 |
| 4,571,182 A * | 2/1986 | Beier et al. | 433/79 |
| 4,715,573 A | 12/1987 | Liegel | |
| 4,725,027 A | 2/1988 | Bekanich | |
| D323,560 S | 1/1992 | Boyce et al. | |
| 5,114,023 A * | 5/1992 | Lavin | 211/107 |
| 5,170,804 A | 12/1992 | Glassman | |
| 5,181,681 A * | 1/1993 | Edwards | 248/125.1 |
| 5,337,992 A | 8/1994 | Pryor et al. | |
| 5,362,021 A | 11/1994 | Phillips | |
| 5,366,191 A | 11/1994 | Bekanich | |
| 5,375,276 A | 12/1994 | Nelson et al. | |
| D363,051 S | 10/1995 | Lanzillo | |
| 5,511,674 A * | 4/1996 | Boyd et al. | 211/70.6 |
| 5,681,018 A | 10/1997 | Hoftman | |
| 5,735,413 A * | 4/1998 | Allen | 211/107 |
| 6,426,041 B1 | 7/2002 | Smith | |
| 6,471,167 B1 | 10/2002 | Myers et al. | |
| D467,754 S | 12/2002 | Chen | |
| 6,629,615 B2 * | 10/2003 | Kim | 211/85.13 |
| 6,968,957 B2 * | 11/2005 | Fynn | 211/11 |
| 7,314,010 B2 | 1/2008 | George et al. | |
| 7,448,099 B2 | 11/2008 | Abernathie | |
| 7,490,837 B2 * | 2/2009 | Pond et al. | 280/47.35 |
| D588,272 S * | 3/2009 | Meiser | D24/185 |
| D588,829 S | 3/2009 | Rheault et al. | |
| 7,540,243 B2 | 6/2009 | George et al. | |
| D606,202 S * | 12/2009 | Banryu | D24/185 |
| 7,665,606 B2 * | 2/2010 | Gaillard | 206/363 |
| 7,676,865 B2 | 3/2010 | Graham et al. | |
| 7,735,788 B2 | 6/2010 | Newkirk et al. | |
| D626,238 S | 10/2010 | Zinnanti | |
| 8,100,061 B2 * | 1/2012 | Hookway et al. | 108/50.01 |
| 8,453,977 B2 * | 6/2013 | Zoland et al. | 248/37.6 |
| 8,613,454 B2 * | 12/2013 | Foley | 280/32.6 |
| 2002/0092816 A1 * | 7/2002 | Kim | 211/85.13 |
| 2003/0101512 A1 | 6/2003 | Jensen et al. | |
| 2003/0233964 A1 * | 12/2003 | Comeaux | 108/90 |
| 2006/0167400 A1 * | 7/2006 | Ellingboe et al. | 604/6.14 |
| 2010/0174415 A1 * | 7/2010 | Humayun et al. | 700/282 |
| 2011/0203957 A1 * | 8/2011 | Zoland et al. | 206/363 |
| 2012/0074034 A1 * | 3/2012 | Bar | 206/562 |
| 2012/0325704 A1 * | 12/2012 | Kerns et al. | 206/370 |

* cited by examiner

US 9,033,162 B2

SYSTEM, METHOD AND APPARATUS FOR SURGICAL STAND

This application claims priority to and the benefit of U.S. Provisional Patent Application No. 61/595,928, filed Feb. 7, 2012, and is incorporated herein by reference in its entirety.

BACKGROUND OF THE INVENTION

1. Field of the Disclosure

The present invention relates in general to surgical stands and, in particular, to an improved system, method and apparatus for a surgical stand.

2. Description of the Related Art

Operating room practices require the equipment used during procedures to remain in a sterile area. The sterile area is defined with respect to a standing person, such as from the vertical region of a scrub assistant from chest to waist. Newer surgical techniques require numerous complicated and potentially hazardous instruments that must be safely managed in the sterile area. For example, surgeons typically place arthroscopes, laparoscopes, lasers, and bovie electrocautery directly on patients during surgery. The light source for the arthroscope, the bovie, and oscillating saws are potential burn or cutting sources for the patient. Yet, these instruments must be placed directly on the patient because they have sterile cords that may be contaminated if placed on a remote back table and brought back and forth from that remote table to the patient's surgical wound where they are used.

In addition, such operating equipment has multiple electric cords and surgical suction tubing that must remain in the midline of the sterile field. The current practice to keep these cords and tubing from migrating peripherally (into non-sterile areas) is to use straps placed on the disposable sterile paper drapes that surround the operative site. With repetitive use during surgery, these cords and tubing may loosen from the straps, fall off the edges of the surgical drapes and contaminate the tubing and cords, as well as the downstream instruments that are being supplied power by the electrical cords. Thus, improvements in managing operating room equipment continue to be of interest.

SUMMARY

Embodiments of a system, method and apparatus for a surgical stand are disclosed. For example, the stand may comprise a support post configured to be oriented in a substantially vertical orientation. A frame extends from the support post and is configured to be oriented in a substantially horizontal orientation. A tray has a first deck that is complementary in shape to the frame and configured to rest on and be supported by the frame. A second deck is connected to and transversely spaced apart from the first deck, such that at least lateral access to both the first and second support surfaces is provided. The tray may be disposable.

The foregoing and other objects and advantages of these embodiments will be apparent to those of ordinary skill in the art in view of the following detailed description, taken in conjunction with the appended claims and the accompanying drawings.

BRIEF DESCRIPTION OF THE DRAWINGS

So that the manner in which the features and advantages of the embodiments are attained and can be understood in more detail, a more particular description may be had by reference to the embodiments thereof that are illustrated in the appended drawings. However, the drawings illustrate only some embodiments and therefore are not to be considered limiting in scope as there may be other equally effective embodiments.

The use of the same reference symbols in different drawings indicates similar or identical items.

DETAILED DESCRIPTION

Figure 1:
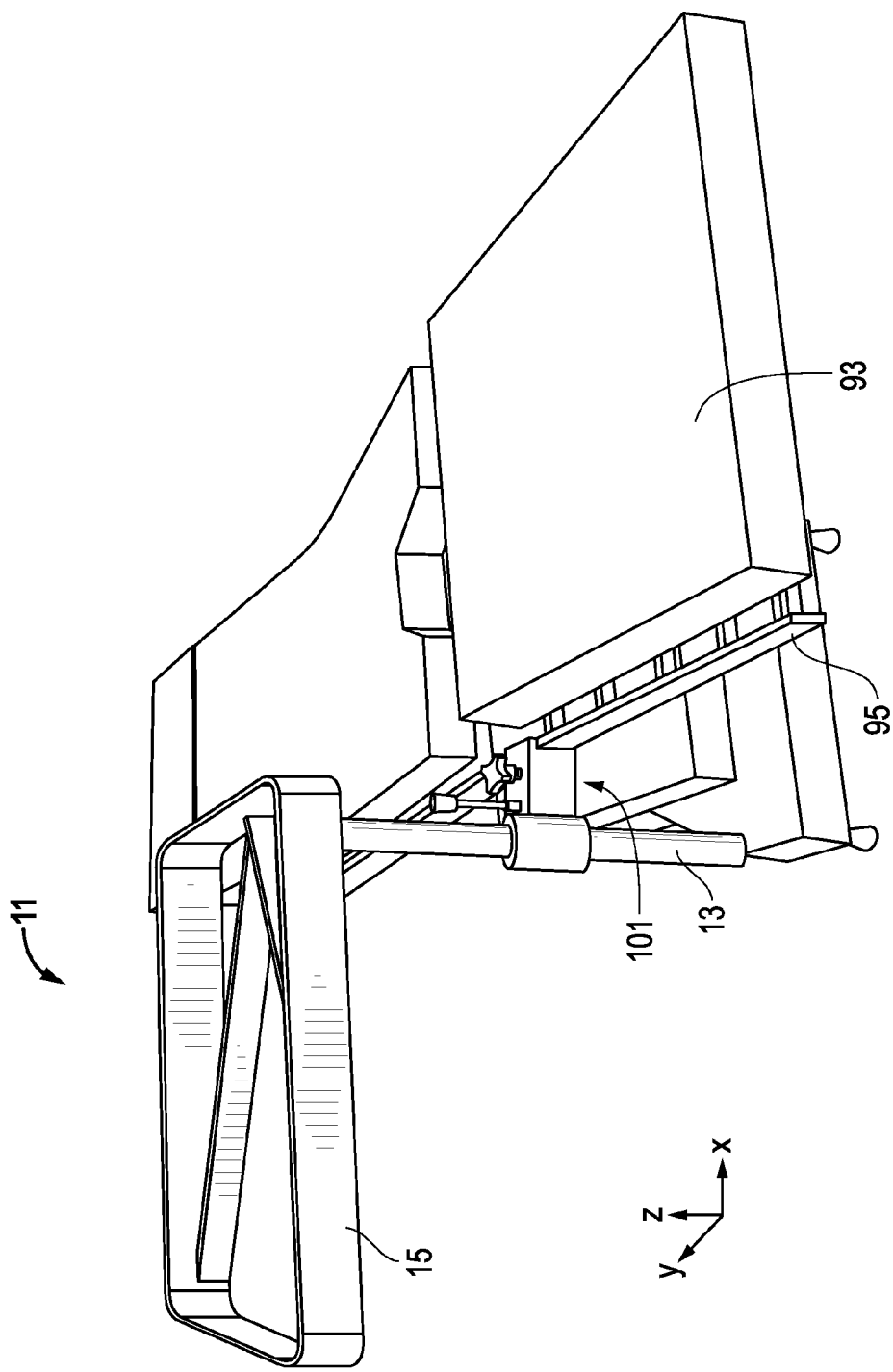
FIG. 1 is an isometric view of an embodiment of a stand.

Embodiments of a system, method and apparatus for a surgical stand are disclosed. For example, the surgical stand 11 (FIG. 1) may comprise a safety instrument platform (SIP) stand having a support post 13 that is configured to be oriented in a substantially vertical orientation. A frame 15 may extend from the support post 13 and be configured to be oriented in a substantially horizontal orientation. Both the support post 13 and frame 15 may be formed from rigid materials, such as metals.

Figure 2:
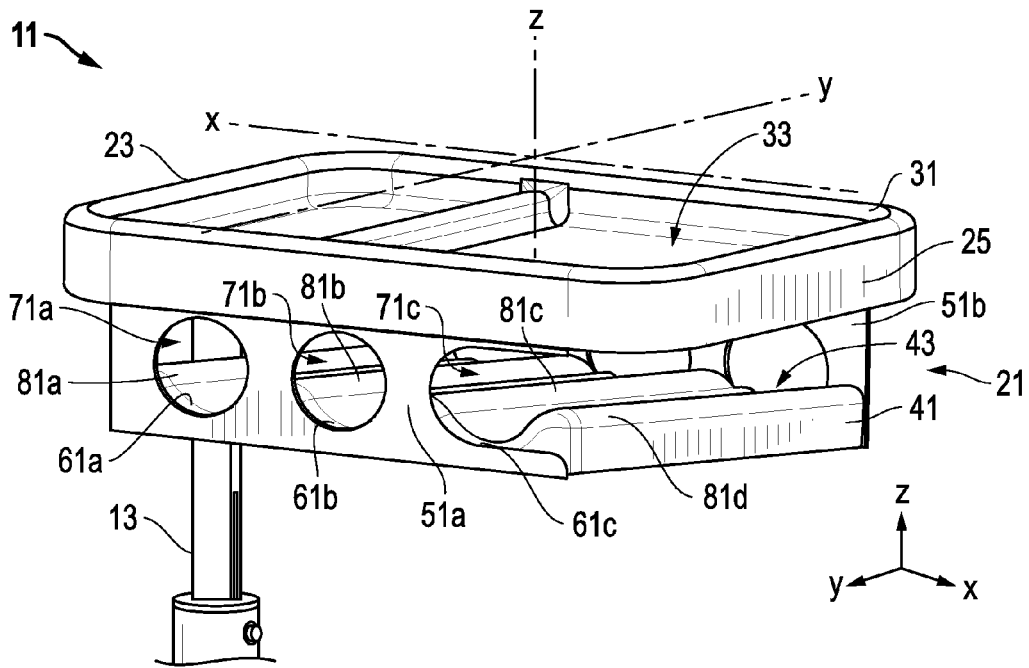
FIGS. 2 and 3 are front and rear isometric views of embodiments of stands with trays.

As shown in FIG. 2, the frame 15 is configured to support a tray 21. The tray may be disposable and formed from a plastic or other suitably safe and inexpensive materials. In some embodiments, the term "disposable" comprises a single-use application. The tray 21 has a proximal end 23 located adjacent the support post 13 and a distal end 25 opposite the proximal end 23. For reference purposes, a longitudinal direction "x" is defined as extending between the proximal and distal ends 23, 25. A lateral direction "y" is perpendicular to the longitudinal direction x, such that both the longitudinal and lateral directions x, y are substantially horizontal. A transverse direction "z" is perpendicular to both the longitudinal and lateral directions x, y such that it is substantially vertical.

Embodiments of the tray 21 may further comprise a first deck 31 that is complementary in shape to the frame 15 and configured to rest on and be supported exclusively by the frame 15. The first deck 31 has a first support surface 33, which may comprise many different forms depending on the surgical application.

A second deck 41 is connected to the first deck 31. The second deck 41 may be substantially longitudinally and laterally aligned with the first deck 31 and have a second support surface 43. The first and second decks 31, 41 may have similar horizontal surface areas (e.g., +/−25%), or substantially the same horizontal surface area. The tray 21 may comprise a single integrated (e.g., molded) component comprising both of the first and second decks, or a plurality of components (e.g., two separate molded components) that are discrete and configured to be assembled together.

The second deck 41 may be transversely spaced apart (i.e., in the z direction) from the first deck 31, such that a user is provided with at least lateral (i.e., in the y-direction) access to both the first and second support surfaces 33, 43. The first deck 31 may provide access in all three of the longitudinal, lateral and transverse directions. The second deck 41 may provide access in substantially only the longitudinal and lateral directions.

In the embodiment shown, the second deck 41 hangs below and is supported exclusively by the first deck 31 (or upper deck), such that the second deck 41 (or lower deck) is directly beneath the frame 15. In this configuration, the second support surface 43 is located entirely beneath the upper deck 41. Alternatively, the second deck 41 may be located above the first deck 31. Although the tray 21 is formed from a disposable material, the first and second decks 31, 41 may be substantially fixed with respect to each other, such that they adequately support tools for surgical procedures with substantially no relative movement therebetween.

The tray 21 may be provided with sidewalls 51 that connect the first deck 21 to the second deck 41. The sidewalls 51 may have the same transverse or z-direction dimension such that both the first and second decks 31, 41 are substantially horizontal. Alternatively, one of the sidewalls 51b (FIG. 3) may have a greater transverse dimension than the other sidewall 51a, such that one of the decks is horizontal (e.g., first deck 31) and the other deck (e.g., second deck 41) is inclined relative to horizontal.

Figure 3:
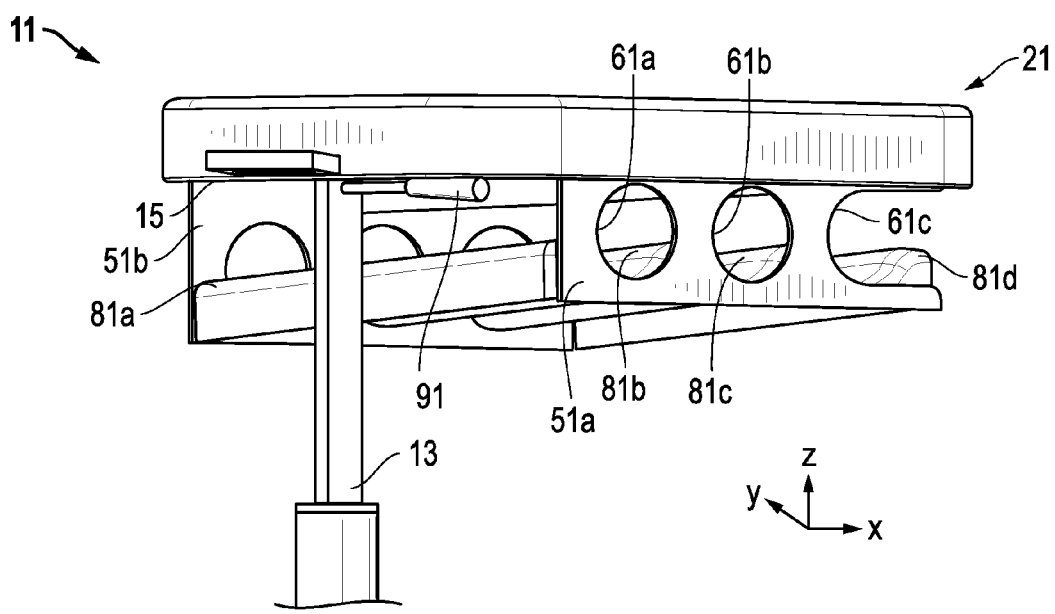

Each of the side walls 51 may be provided with a plurality of apertures 61 (e.g., three shown) that are configured to receive and support medical equipment. In the example of FIG. 3, the apertures 61a and 61b may be circular, and a distal one of the apertures 61c may be semi-circular.

The second deck 41 may be provided with a plurality of bays 71a, 71b, 71c that extend in the lateral or y-direction. The bays 71a-c may be longitudinally aligned with respective ones of the apertures 61a-c. The bays 71 may be partitioned by baffles 81 and each of the bays 71 may be semi-cylindrical in shape. The second deck 41 may further comprise end baffles 81a, 81d on its longitudinal ends (i.e., proximal and distal ends).

Each of the apertures 61 may be configured to provide ingress and egress of medical equipment in the lateral or y-direction. For example, equipment such as scopes, shavers, lasers, etc., may be placed in through one or more of the apertures 61 on the second support surface 43. Other ones of the apertures 61 may support and provide control for tubing and cords, such as surgical suction tubing and sterile electric cords. The distal one of the apertures 61c has an open structure that is configured to provide ingress and egress of medical equipment in both the longitudinal and lateral directions.

Figure 4:
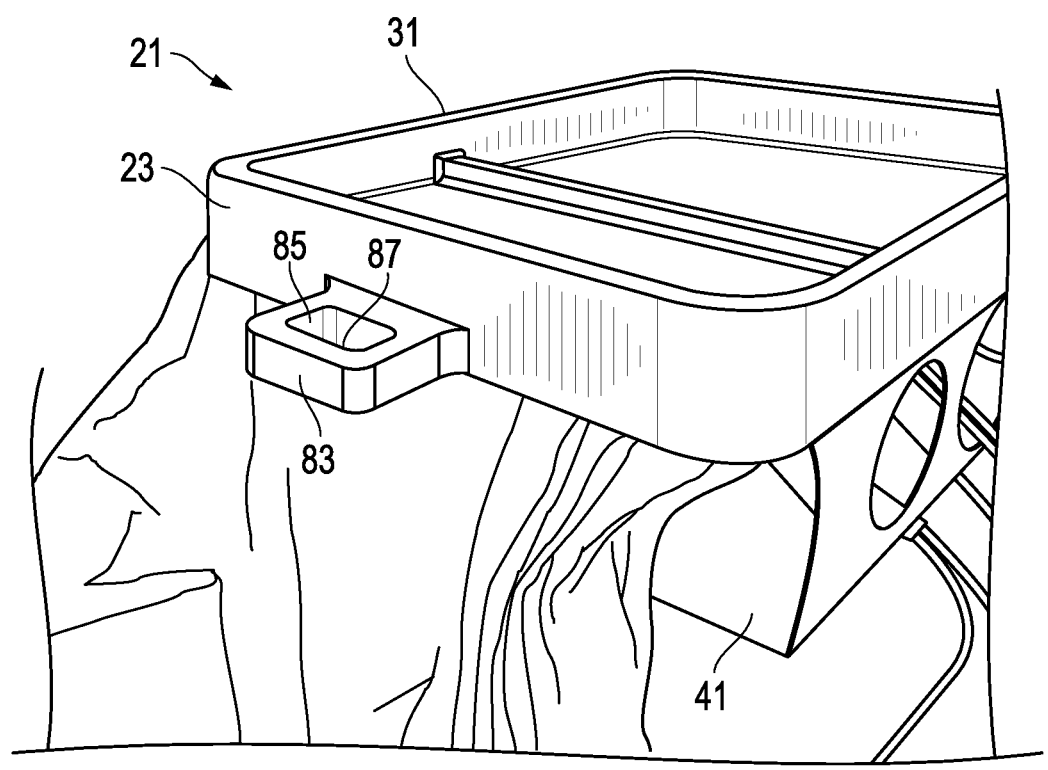
FIGS. 4-6 are side and rear isometric views of alternate embodiments of stands with trays.

The tray 21 may further comprise a pocket 83 (FIG. 4) extending from tray. The pocket 83 may have a profile 85 and open slot 87 that are configured to support medical equipment. The pocket 83 may be located on the first deck 31 and may extend longitudinally from the proximal end 23 of the tray 21. The profile 85 and open slot 87 of the pocket 83 may be rectangular in shape and adapted to support bovie holsters having either oval or rectangular shapes.

Again referring to FIG. 3, the stand 11 may further comprise a lever 91 configured to adjust a vertical or transverse position (i.e., in the z-direction) of the frame 15 and tray 21 relative to an operating room table 93. The lever 91 may extend from the support post 13 and may be located beneath the frame 15 between the first and second decks 31, 41.

Figure 5:
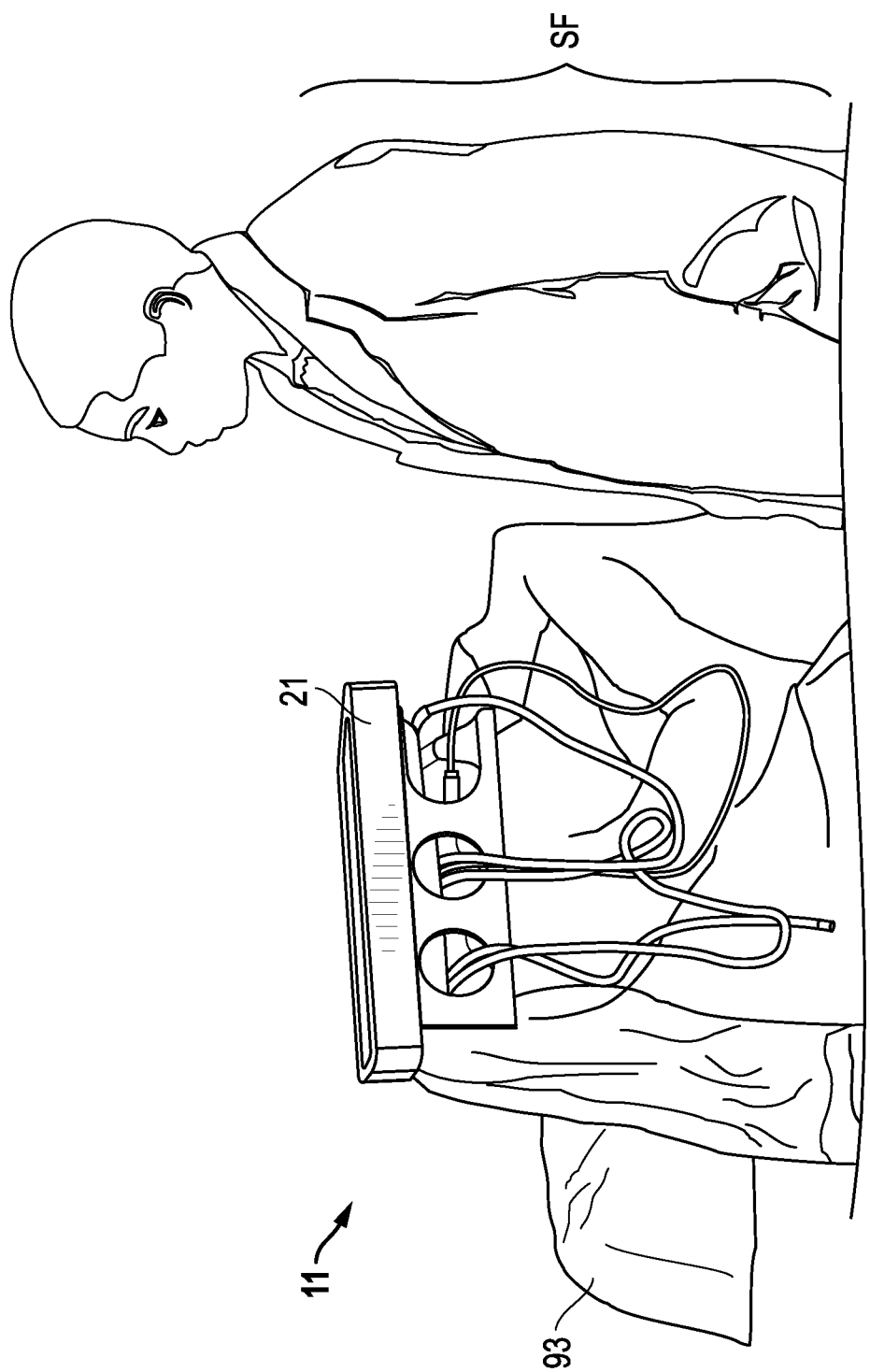

The lever 91 is located in a sterile field SF (FIG. 5) as defined by current operating room practice. The SF extends in the transverse or z-direction between a chest and a waist of a person standing in the room, such as a scrub assistant. Lever 91 is located on the stand 11 to meet this sterile area criteria, which allows for adjustments to its height by a "sterile" scrub tech or nurse who is "sterile" (i.e., scrubbed in the case). Thus, an operating room nurse can deploy lever 91 and move the stand 11 up or down. If lever 91 was down at the attachment site of the stand 11 to the rail 95 of the operating room table 95, the adjustments would have to be made by a non-sterile person in the operating room. Lever 91 may be covered by a sterile mayo stand cover but is in the correct sterile area.

Figure 6:
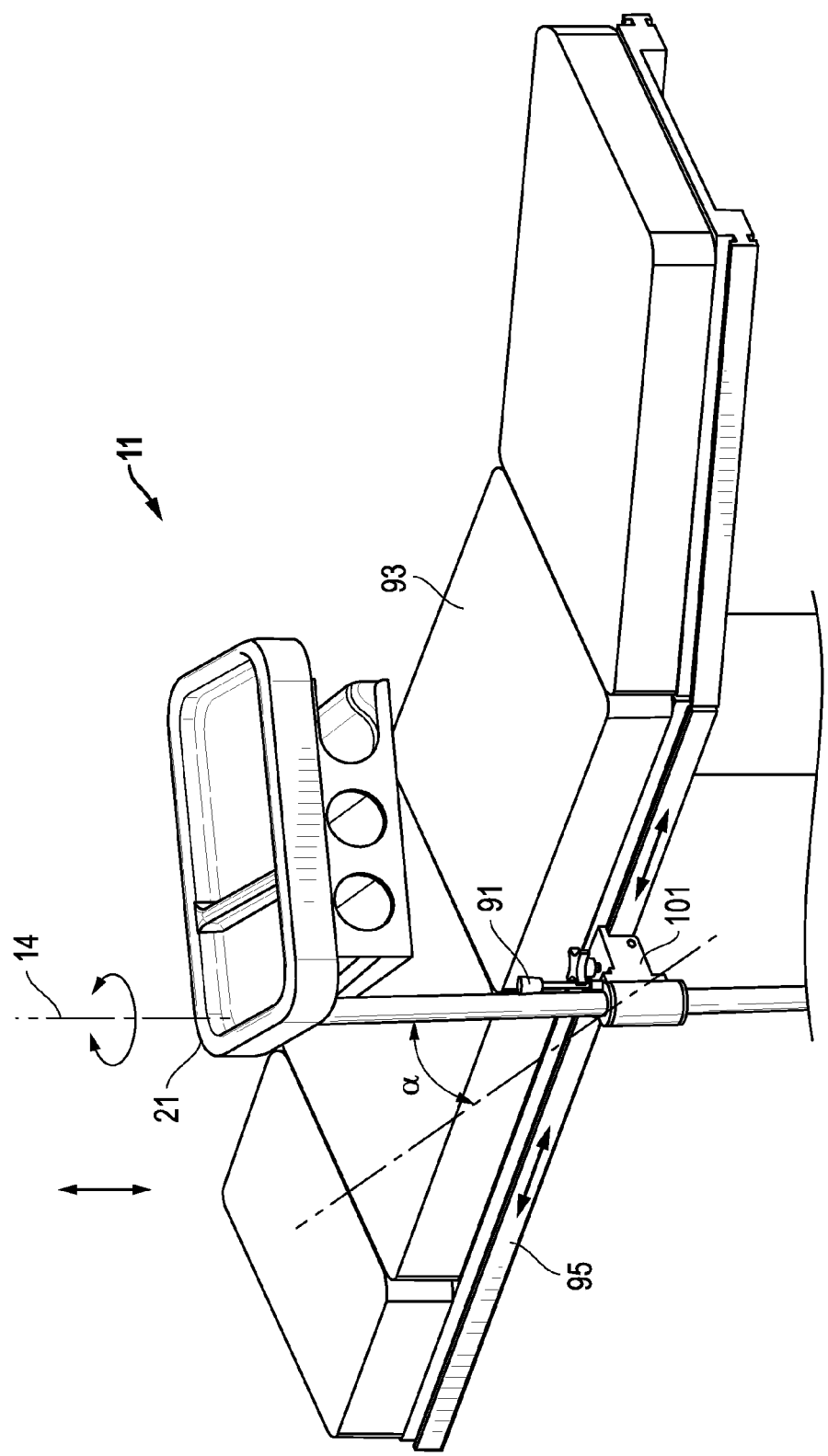
Figure 7:
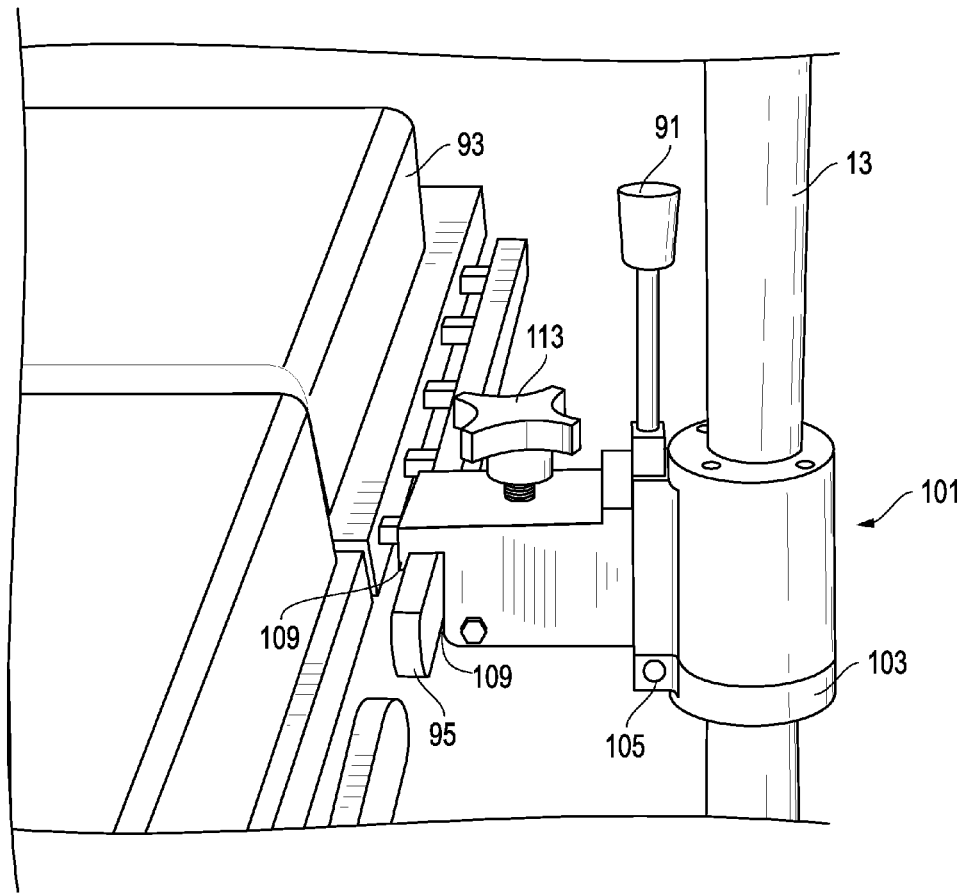
FIGS. 7 and 8 are enlarged isometric views of embodiments of a bracket for a stand.
Figure 8:
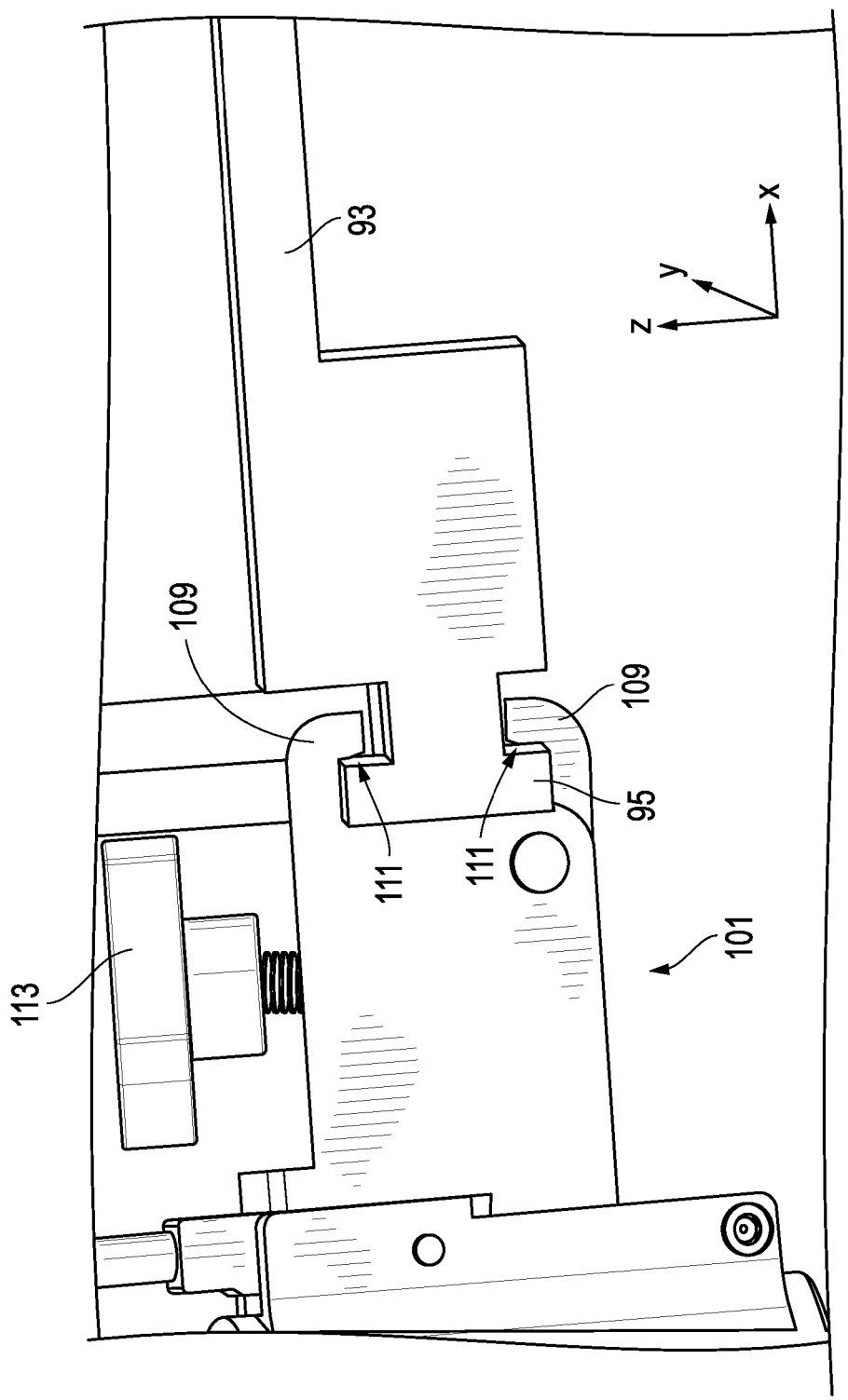

The stand 11 also may further comprise a mounting bracket 101 (FIGS. 6-8) that is configured to mount the support post 13 to a rail 95, such as a table rail. The frame 15 and tray 21 are collectively rotatable (FIG. 6, circular arrow) about an axis 14 of the support post 13. In some embodiments, rotation of the frame 15 and tray 21 is frictionally limited by controlled drag in the mounting bracket 101. A desired amount of drag may be provided by a sleeve 103 (FIG. 7) on or inside the mounting bracket 101. The mounting bracket 101 may adjustably compress the sleeve 103 (e.g., via a screw 105) in a radial direction relative to the axis 14 to provide a variable amount of drag on rotation of the support post 13. If the tray were bumped or rotated without drag control, the heavy instruments on the tray could be thrown off of the tray onto the patient. A lack of drag control also may permit annoying rotational migration of the tray during surgery.

In some embodiments, the drag feature acts as a brake that is fully adjustable from "off" (no drag/no brake, such that the stand may free wheel) to fully "on" (locked like an emergency brake) to anywhere in between, where the "brake" is partially applied resulting in the desired drag to allow movement but to prevent unintended movement. The coefficient of friction in this joint may be tuned and varied based on the application of use, manufacturing tolerances and surface finishes.

The mounting bracket 101 may further comprise a lever 91 (e.g., a tilt lever) that is configured to variably adjust an angle of inclination a of the support post 13 in a vertical plane to either side of the table 93. The mounting bracket 101 may still further comprise a clamp with jaws 109 (FIG. 8) configured to adjustably grip the rail 95. The jaws 109 may comprise inner surfaces 111 that are inclined toward the table 93, or relative to a vertical plane defined by the lateral and transverse directions, y and z. The inner surfaces 111 are adapted to draw the rail 95 into the jaws 109 when the jaws are tightened (e.g., via mechanism 113), thereby always ensuring a snug fit even after normal wear. Thus, jaws 109 thoroughly compensate for the equipment on the tray that generates significant cantilever forces on the stand to avoid swaying or other dangerous instabilities. Mounting bracket 101 also provides lateral repositioning (see horizontal arrows in FIG. 6) of the support post 13, frame 15 and tray 21 along rail 95.

Figure 9:
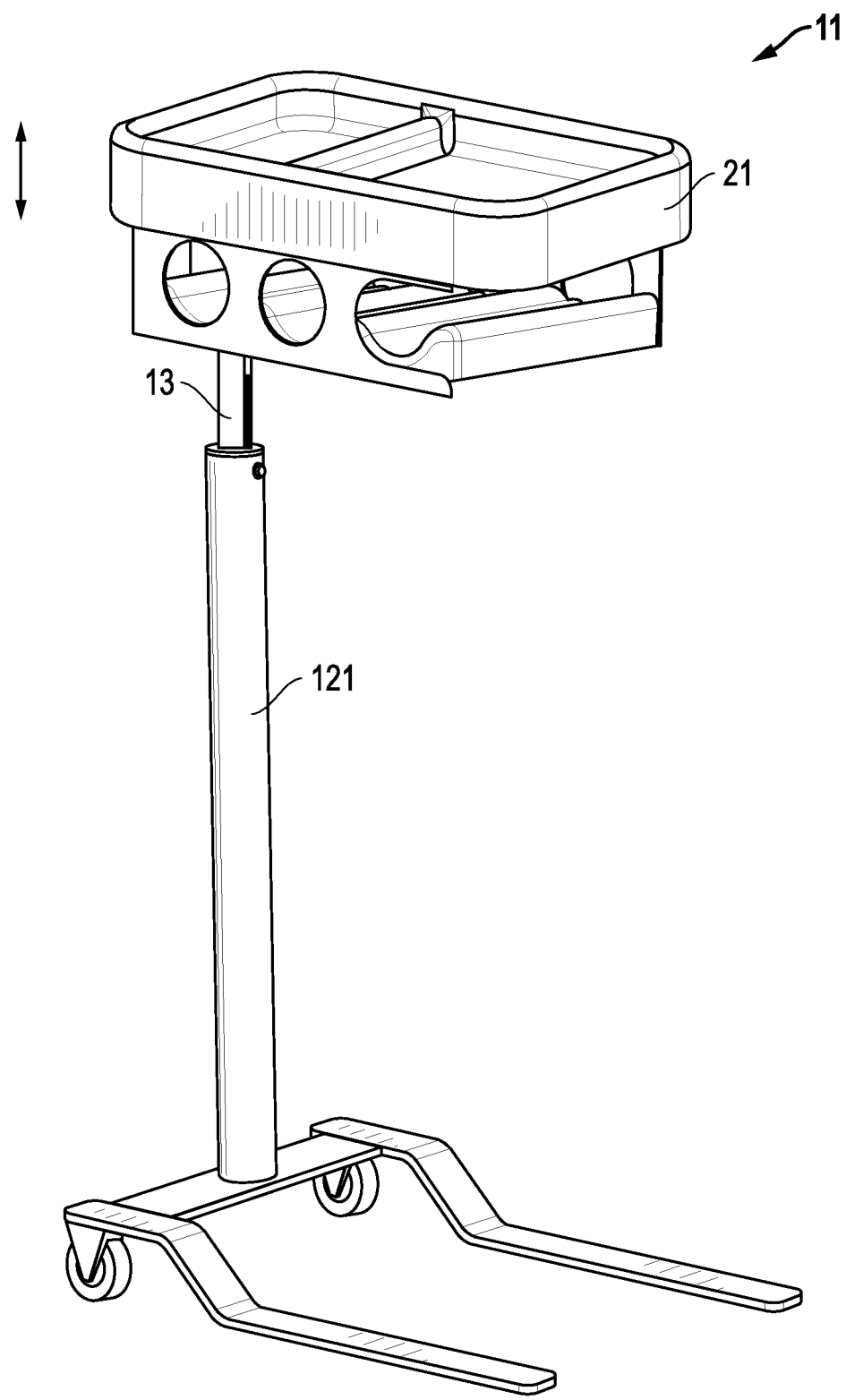
FIGS. 9 and 10 are isometric views of other embodiments of stands and trays.

In still other embodiments, the stand may further comprise a portable floor base 121 (FIG. 9), such as a Mayo stand, which is configured to engage and mount the support post 13 as shown. Thus, stand 11 may be mounted to table 93 or portable floor base 121.

Figure 10:
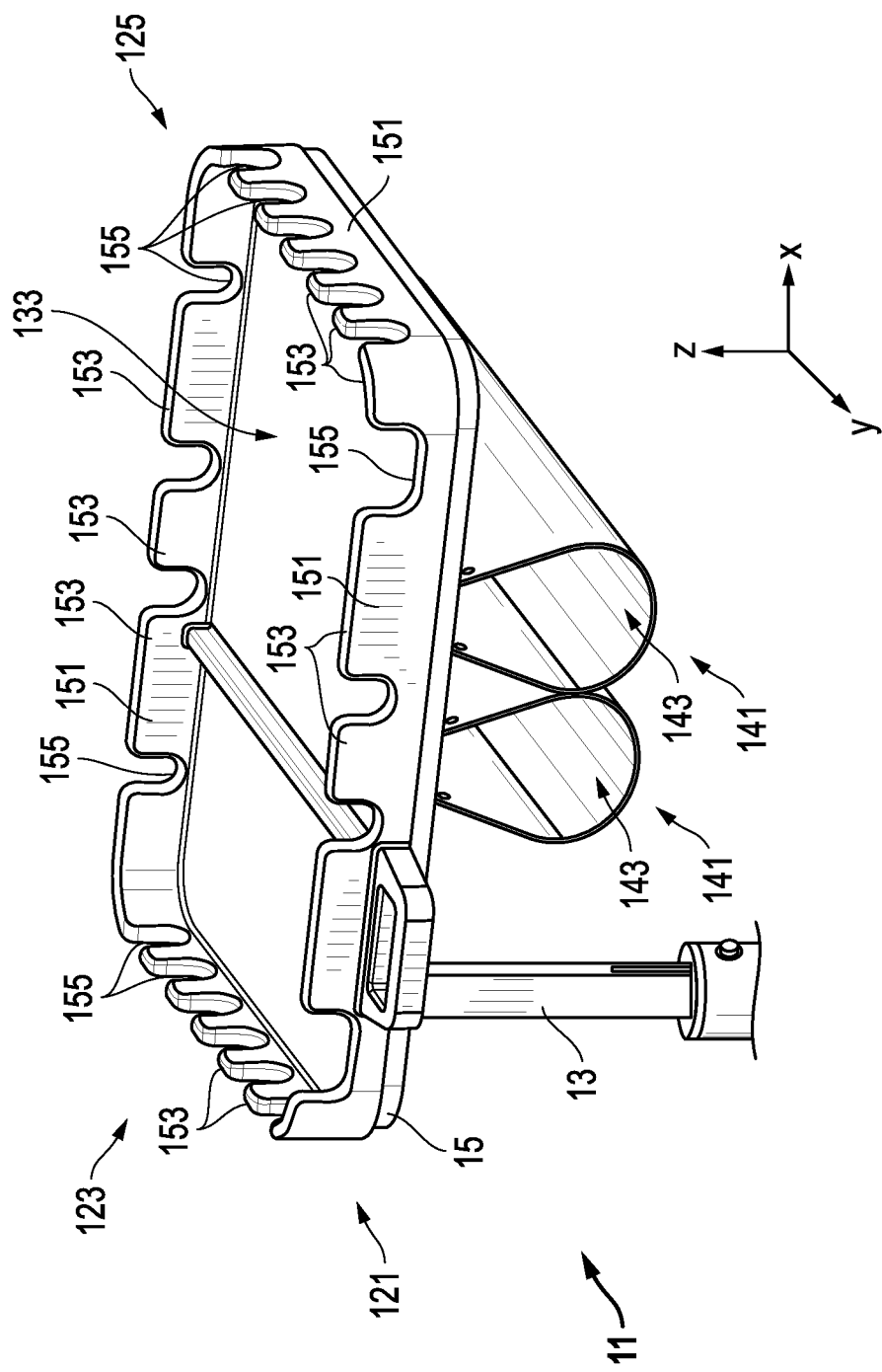
Figure 11:
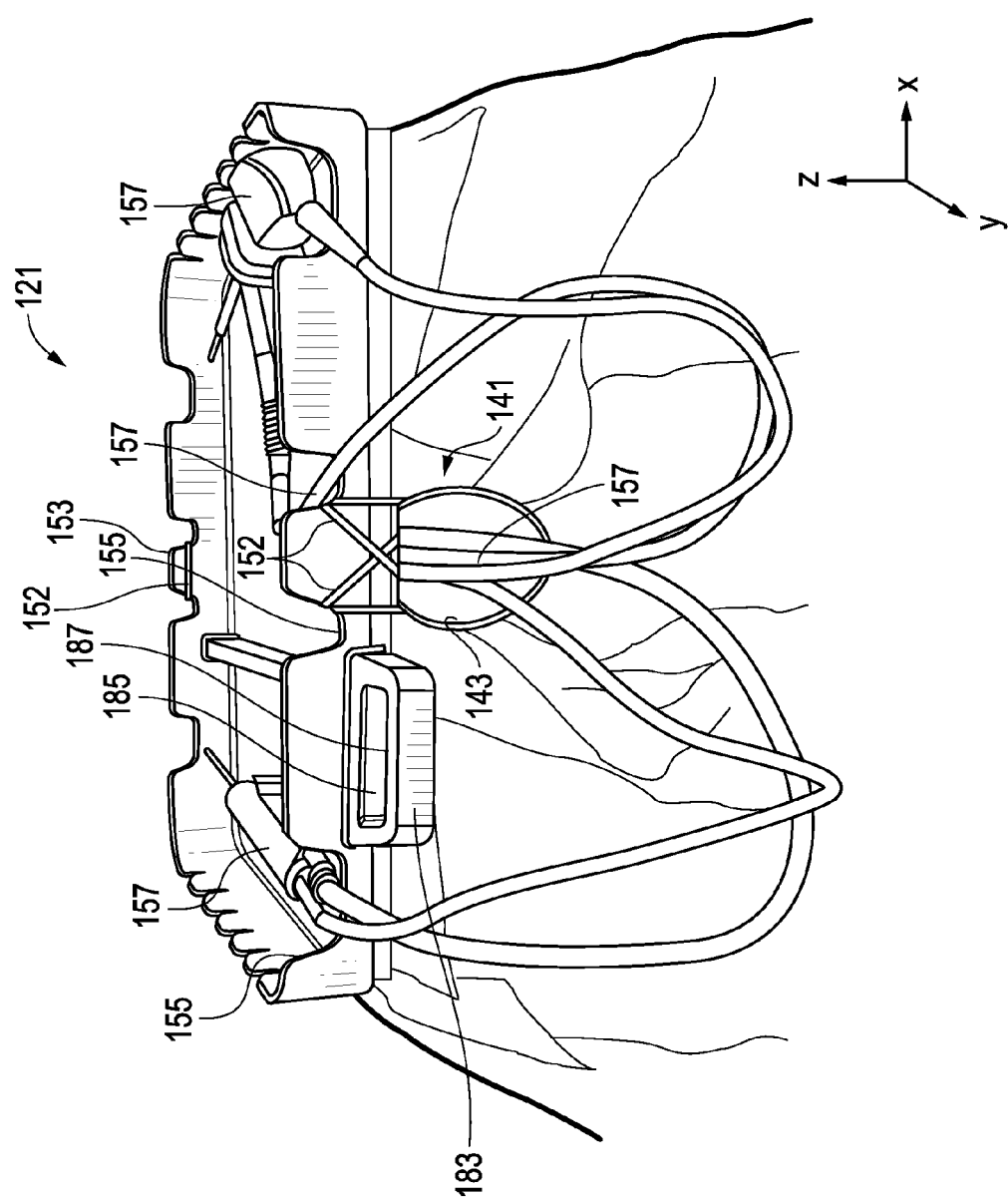
FIG. 11 is an isometric view of an embodiment of a tray and stand in operation.

Referring now to FIGS. 10 and 11, still other embodiments of a tray 121 and a surgical stand 11 are shown. The tray 121 and surgical stand 11 may be configured as described elsewhere herein for the various embodiments. The tray 121 has a proximal end 123 located adjacent the support post 13 and a distal end 125 opposite the proximal end 123. Embodiments of the tray 121 may comprise a first deck 131 that is complementary in shape to the frame 15 of stand 11, and configured to rest on and be supported exclusively by the frame 15. The first deck 131 has a first support surface 133, which may comprise many different forms depending on the surgical application.

One or more second decks 141 (e.g., two shown) may be connected to the first deck 131. The second deck 141 may be tubular and substantially lateral, and may include a second support surface 143. The tray 121 may comprise a plurality of separate, discrete components (e.g., the three separately molded components shown) that are configured to be assembled together.

The second deck(s) 141 may be transversely spaced apart (i.e., in the z-direction) from the first deck 131, such that a user is provided with at least lateral (i.e., in the y-direction) access to both the first and second support surfaces 133, 143. The first deck 131 may provide access in all three of the longitudinal, lateral and transverse directions. The second deck 141 may provide access in substantially only the lateral direction.

In the embodiment shown, the second deck 141 may hang below and may be supported exclusively by the first deck 131 (or upper deck), such that the second deck 141 (or lower deck) is directly beneath the frame 15. In this configuration, the second support surface 143 is located entirely beneath the upper deck 131. Although the tray 121 may be formed from disposable materials, the first and second decks 131, 141 may be substantially fixed with respect to each other, such that they are adequately rigid enough to support tools for surgical procedures with substantially no relative movement therebetween.

The tray 121 may be provided with sidewalls 151. As shown in FIG. 11, the sidewalls 151 may be used to connect the first deck 121 to the second deck 141, such as via elastic bands 152 (e.g., rubber bands). For example, one elastic band 152 may extend along each lateral edge of second deck 141 and protrude from holes on both ends thereof. Thus, only two elastic bands 152 may be used to adequately secure second deck 141 to first deck 121. The ends of the elastic bands 152 may wrap around and be secured to features in sidewalls 151, such as castellations 153. The castellations 153 may define apertures 155 therebetween. The apertures 155 may vary in shape and size, depending on the application. As shown in FIG. 12, apertures 155 are well suited for supporting and separating various types of devices and cords 157 on or in tray 121 Likewise, second support surface 143 of second deck 141 is well suited for supporting various types of devices and cords 157.

Embodiments of second deck 141 may be configured to provide ingress and egress of medical equipment in the lateral or y-direction. For example, equipment such as scopes, shavers, lasers, etc., may be placed in or through the second support surface 143. The first and second decks 121, 141, castellations 153 and apertures 155 may support and provide control for tubing and cords, such as surgical suction tubing and sterile electric cords. Each of these components may be configured with an open structure to provide ingress and egress of medical equipment in one or more of the longitudinal, lateral and transverse directions.

The sidewalls 151 may have the same transverse or z-direction dimension such that both the first and second decks 131, 141 are substantially horizontal. Alternatively, one of the sidewalls 151 may have a greater transverse dimension than the other sidewall 151, such that one of the decks is horizontal and the other deck is inclined relative to horizontal. The sidewalls 151 may be further configured as described elsewhere herein.

The tray 121 may further comprise a pocket 183 extending from tray. The pocket 183 may have a profile 185 and open slot 187 that are configured to support medical equipment as described elsewhere herein. The pocket 183 may extend in any direction, but is shown extending in the lateral direction from first deck 131. The profile 185 and open slot 187 of the pocket 183 may be rectangular in shape and adapted to support bovie holsters having either oval or rectangular shapes.

Still other embodiments of a stand may comprise a support post configured to be oriented in a substantially vertical orientation. A frame may extend from the support post and be configured to be oriented in a substantially horizontal orientation. A tray that is disposable has a proximal end located adjacent the support post and a distal end opposite the proximal end. A longitudinal direction extends between the proximal and distal ends. A lateral direction is perpendicular to the longitudinal direction, such that both the longitudinal and lateral directions are substantially horizontal. A transverse direction perpendicular to both the longitudinal and lateral directions is substantially vertical.

The tray may further comprise a first deck that is complementary in shape to the frame and configured to be supported by the frame. The first deck may have a first support surface. A second deck may be connected to the first deck. The second deck may have a second support surface that is transversely spaced apart from the first deck, such that at least lateral access to both the first and second support surfaces is provided. The first deck may provide access in the longitudinal, lateral and transverse directions, and the second deck may provide access in substantially only the lateral direction. The second deck may hang below and be supported by the first deck, such that the second deck is beneath the frame. The tray may be plastic, and the first and second decks may be substantially fixed with respect to each other. The tray may have sidewalls having apertures configured to receive and support medical equipment. The second deck may comprise a plurality of second decks that are longitudinally spaced apart from each other. The first and second decks may be separate, discrete components configured to be assembled together, such as by rubber bands.

The stand may further comprise a lever configured to adjust a vertical position of the frame and tray. The lever may be located in a sterile field. The sterile field may be defined in the transverse direction between a chest and a waist of a standing person. The lever may extend from the support post and be located beneath the frame between the first and second decks.

The stand may further comprise a mounting bracket configured to mount the support post to a rail. The frame and tray may be collectively rotatable about an axis of the support post. Rotation of the frame and tray may be frictionally limited by a brake in the mounting bracket configured to adjustably exert drag on the support post.

The stand may further comprise a pocket extending from tray. The pocket may have a profile and open slot configured to support medical equipment. The pocket may be located on the first deck and extend substantially horizontally from the tray. The profile and open slot of the pocket may be rectangular in shape and adapted to support bovie holsters having either oval or rectangular shapes.

Additional embodiments of the tray may comprise a first deck having a first support surface to provide access in the longitudinal, lateral and transverse directions. A second deck may be connected to and transversely spaced below the first deck. The second deck may have a second support surface that provides access in substantially only the lateral direction. The tray may be disposable.

The second support surface may be located beneath the first deck. The tray may have sidewalls that support the second deck. The sidewalls may have apertures configured to receive and support medical equipment. The second deck may comprise a plurality of tubular second decks that extend in the lateral direction. The first and second decks may be discrete components that are configured to be assembled together.

The tray may further comprise a pocket extending from tray. The pocket may have a profile and open slot configured to support medical equipment. The pocket may be located on the first deck and extend laterally from the tray. The profile and open slot of the pocket may be rectangular in shape and may be adapted to support bovie holsters having either oval or rectangular shapes.

The embodiments disclosed herein have numerous advantages compared to conventional solutions. With the advent of newer surgical techniques and instruments, the safety of current operating room practices can be improved. Presently, surgeons lay arthroscopes, laparoscopes, lasers, and bovie electrocautery directly on the patient during surgery. The light source for the arthroscope, the bovie, and oscillating saws are all potential burn or cutting sources for the patient, and yet these instruments are typically placed directly on the patient. This is necessitated since these tools have sterile cords that would become contaminated if they were placed on a remote or back table and brought back and forth from that table to the surgical wound of the patient where they are used. The stand and tray described herein places traditional and possibly injurious operating instruments (e.g., scalpel and suture needles) and the bovie electrocautery on the upper deck of the tray. Surgical instruments such as scopes, shavers, lasers, etc., may be placed in the lower deck of the tray. Such designs prevent the burn/cutting/sawing instruments from being placed directly on the patient's torso face or extremities. Ergonomically, the tray also allows the operating room technician to pass instruments from the immediate area that the surgery is actually taking place, rather than from a back table which is several feet from the area the surgery is occurring.

The embodiments disclosed herein also address issues related to the electrical cords and surgical suction tubing that must remain in the midline of the horizontal sterile field. Unfortunately, the current practice is to try to keep these cords and tubes from migrating peripherally (into non-sterile areas) with straps placed on the disposable sterile paper drapes that surround the operative site. With repetitive use during surgery, the cords and tubes may break loose from the straps and fall off the edges of the surgical drapes, thereby contaminating the cords, tubes as well as the downstream instruments that are being supplied power by the electrical cords. The middle aperture of the lower deck may thus contain and control these sterile electrical cords and suction tubes and prevents peripheral migration and subsequent contamination at the edges of the sterile operative field.

The pocket on the upper deck of the tray has a slot that fits the two most commonly shaped types of bovie holsters (i.e., oval and rectangular). This allows the burning electrocautery and its protective plastic holster to be up on the tray rather than attached to the drapes directly above the patients torso or head. This feature eliminates another potential burn source to the patient.

Arthroscopes typically have a water inflow attachment, a light cord, and a power cord. The open bay at the distal end of the lower deck of the tray allows the scope and its three attachments (that come off the scope at 90 degree angles) to be easily put in and out of the lower deck of the tray. The open bay accommodates all of the cords and attachments coming off at 90 degree angles from the scope. It is advantageous to have the scope stored in the tray rather than on the sterile drapes adjacent to the patient's body. The light source that comes into the side of the scope and out of the scope tip is extremely bright and hot, which it a potential burn source if placed directly on the sterile drapes over the patient.

Thus, the embodiments disclosed herein eliminate most of the burn perils to underlying unconscious patients, as well as saw/cutting perils from the oscillating saws used in newer techniques and pinching/cutting from the arthroscope shavers. They also maintain cords and suction tubing in the sterile midline of the surgical field. This lowers the infection rate compared to strapped tubing and cords, which can migrate off the sterile field and then inadvertently pull germs back into the sterile field when the surgeon pulls the cords back into the surgical field not knowing they had migrated peripherally into a contaminated peripheral position.

One or ordinary skill in the art will recognize that the embodiments are suitable for many different types of medical applications, including dental applications.

This written description uses examples to disclose the embodiments, including the best mode, and also to enable those of ordinary skill in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A stand, comprising:
a support post configured to be oriented in a substantially vertical orientation;
a frame extending from the support post and configured to be oriented in a substantially horizontal orientation;
a tray that is plastic and disposable and has a proximal end located adjacent the support post and a distal end opposite the proximal end, a longitudinal direction extends between the proximal and distal ends, a lateral direction is perpendicular to the longitudinal direction, such that both the longitudinal and lateral directions are substantially horizontal, and a transverse direction perpendicular to both the longitudinal and lateral directions that is substantially vertical; and the tray further comprises:
a first deck that is complementary in shape to the frame and configured to be supported by the frame, the first deck having a first support surface; and
a second deck connected to the first deck, the second deck having a second support surface that is transversely spaced apart from the first deck, such that at least lateral access to both the first and second support surfaces is provided.

2. A stand according to claim 1, wherein the first deck provides access in the longitudinal, lateral and transverse directions, and the second deck provides access in substantially only the lateral direction.

3. A stand according to claim 1, wherein the second deck hangs below and is supported by the first deck, such that the second deck is directly underneath the frame.

4. A stand according to claim 1, wherein the first and second decks are substantially fixed with respect to each other.

5. A stand according to claim 1, wherein the tray has sidewalls having circular holes configured to receive and support medical equipment.

6. A stand according to claim 1, wherein the second deck comprises a plurality of tubular second decks that are longitudinally spaced apart from each other.

7. A stand according to claim 1, wherein the first and second decks are separate, discrete components configured to be assembled together.

8. A stand according to claim 1, further comprising an adjustable lever configured to adjust a vertical position of the frame and tray, and the lever is configured to be located in a sterile field, wherein sterile field is defined in the transverse direction between a chest and a waist of a standing person.

9. A stand according to claim 8, wherein the lever extends from the support post and is located beneath the frame between the first and second decks.

10. A stand according to claim 1, further comprising a mounting bracket configured to mount the support post to a rail, and the frame and tray are collectively rotatable about an axis of the support post, and rotation of the frame and tray is frictionally limited by a brake in the mounting bracket configured to adjustably exert drag on the support post.

11. A stand according to claim 1, further comprising a pocket extending from tray, the pocket having a profile and open slot configured to support medical equipment.

12. A stand according to claim 11, wherein the pocket is located on the first deck and extends substantially horizontally from the tray.

13. A stand according to claim 11, wherein the profile and open slot of the pocket are rectangular in shape and adapted to support bovie holsters having either oval or rectangular shapes.

14. A tray, comprising:
a proximal end located adjacent the support post and a distal end opposite the proximal end, a longitudinal direction extends between the proximal and distal ends, a lateral direction is perpendicular to the longitudinal direction, such that both the longitudinal and lateral directions are substantially horizontal, and a transverse direction perpendicular to both the longitudinal and lateral directions that is substantially vertical;
a first deck having a first support surface, and the first deck provides access in the longitudinal, lateral and transverse directions;
a second deck connected to and transversely spaced below the first deck, the second deck having a second support surface that provides access in substantially only the lateral direction, the second support surface is located directly underneath the first deck, the tray has sidewalls that support the second deck, and the side walls have circular holes configured to receive and support medical equipment, and the second deck comprises a plurality of tubular second decks that extend in the lateral direction;
the tray is plastic and disposable; and
the first deck provides access in the longitudinal, lateral and transverse directions, and the second deck provides access in substantially only the lateral direction.

15. A tray according to claim 14, wherein the first and second decks are discrete components that are configured to be assembled together.

16. A tray according to claim 14, further comprising a pocket extending from tray, the pocket having a profile and open slot configured to support medical equipment.

17. A tray according to claim 16, wherein the pocket is located on the first deck and extends laterally from the tray.

18. A tray according to claim 16, wherein the profile and open slot of the pocket are rectangular in shape and adapted to support bovie holsters having either oval or rectangular shapes.

* * * * *